United States Patent [19]

Tessler et al.

[11] Patent Number: 4,732,710
[45] Date of Patent: Mar. 22, 1988

[54] PROCESS FOR THE PREPARATION OF AN ANHYDROUS AND AQUEOUS 3-CHLORO-2-SULFOPROPIONIC ACID REAGENT AND ISOLATION OF THE CRYSTALLINE ACID

[75] Inventors: Martin M. Tessler, Edison; Dennis V. Neigel, Whitehouse Station, both of N.J.

[73] Assignee: National Starch and Chemical Corporation, Bridgewater, N.J.

[21] Appl. No.: 553,463

[22] Filed: Nov. 21, 1983

Related U.S. Application Data

[60] Division of Ser. No. 306,129, Sep. 28, 1981, Pat. No. 4,438,047, which is a continuation-in-part of Ser. No. 208,371, Nov. 19, 1980, abandoned.

[51] Int. Cl.[4] ............................................ C07C 143/02
[52] U.S. Cl. .................................................. 260/513 R
[58] Field of Search ..................................... 260/513 R

[56] References Cited

U.S. PATENT DOCUMENTS 2,895,987  7/1959  Hendry ............................... 260/512

OTHER PUBLICATIONS

A. Le Berre et al., No. 397–Acides α–Sulfocarboxyliques et Derives. III.–Sulfonation et Chlorosulfonylation des Acides Acrylique et Chloro—3 Propionique, Bull. Soc. Chim. Fr. (7–8), 2266 (1973), including translation.

Primary Examiner—Alan Siegel
Attorney, Agent, or Firm—Margaret B. Kelley; Edwin M. Szala

[57] ABSTRACT

An improved and novel process for the preparation of an aqueous 3-chloro-2-sulfopropionic acid reagent involves the formation of a reaction mixture by adding acrylic acid to chlorosulfonic acid maintained at about 45° to 130° C., maintaining the mixture at about 60°–130° C. for about 2–6 hours, and adding sufficient water to the resulting anhydrous reagent to decompose the unreacted chlorosulfonic acid and dilute the reagent to a solids content of about 50–95%, preferably 70–90%. The reagent may be vacuum stripped to remove residual hydrochloric acid. Crystalline 3-chloro-2-sulfopropionic acid may be isolated from the aqueous reagent at a solids content above 80% and below 95%, preferably at 85%.

3 Claims, No Drawings

PROCESS FOR THE PREPARATION OF AN ANHYDROUS AND AQUEOUS 3-CHLORO-2-SULFOPROPIONIC ACID REAGENT AND ISOLATION OF THE CRYSTALLINE ACID

This application is a division of Ser. No. 306,129, filed Sep. 28, 1981, now U.S. Pat. No. 4,438,047, which is a continuation-in-part of Ser. No. 208,371, filed Nov. 19, 1980, now abandoned.

BACKGROUND OF THE INVENTION

This invention relates to an improved process for preparing a liquid anhydrous 3-chloro-2-sulfopropionic acid reagent from acrylic acid and chlorosulfonic acid. It also relates to a novel process for preparing an aqueous reagent which is easily pourable at temperatures below 25° C. It further relates to the isolation of 3-chloro-2-sulfopropionic acid in crystalline form.

The technical literature reveals two basic processes for preparing 3-chloro-2-sulfopropionic acid reagents. One involves the sulfonation of 3-chloropropionic acid with sulfur trioxide (see Bull. Soc. Chim. Fr. (7–8), Part 2, 2266, 1973); the other involves the reaction of acrylic acid and chlorosulfonic acid (see Bull. Soc. Chim. Fr. cited above and U.S. Pat. No. 2,895,987).

The sulfonation process requires the addition, with cooling, of 3-chloropropionic acid to liquid sulfur trioxide. The mixture is then homogenized, heated to 80° C. and maintained at 80° C. for 24 hours, and cooled. The resulting syrupy mass contains about 90% 3-chloro-2sulfopropionic acid, 3.5% unreacted 3-chloropropionic acid, and 6.5% sulfur trioxide. This process suffers from several drawbacks, namely one of the reagents is relatively expensive (i.e. 3-chloropropionic acid) and the other is difficult to handle (i.e. sulfur trioxide). Also it requires reagent addition at low temperatures, homogenization, and slow heating to the final reaction temperature.

The process described in the above cited U.S. patent reveals the 3-chloro-2-sulfopropionic acid as an intermediate which is not isolated. A half mole of chlorosulfonic acid is added dropwise to acrylic acid, the dropwise addition being necessary since rapid addition causes the temperature to rise to about 145° C. The mixture is then cooled to 80° C., the remaining chlorosulfonic acid is added at this temperature over about 10–15 minutes, and the mixture is stirred for 2 hours at 65° to 90° C. and then cooled.

The process wherein chlorosulfonic acid is added to acrylic acid is a potentially very dangerous process for large scale reactions. The reagent addition is an extremely exothermic reaction, and it requires cooling and very slow chlorosulfonic acid addition, followed by slow heating to the reaction temperature (80° C.). If the temperature becomes too high during the addition or if the reaction mixture is heated too rapidly to 80° C., the mixture rapidly increases in temperature (to above 150° C.) and the final product can form as an insoluble rubbery mass (probably polyacrylic acid).

The other process described in the French journal involves the addition of acrylic acid to chlorosulfonic acid maintained at 0° to 10° C. The mixture is then heated slowly to 80° C., maintained at that temperature for 20 hours, and cooled. The resulting reagent contains about 90% 3-chloro-2-sulfopropionic acid, 2% 3-chloropropionic acid, and 8% chlorosulfonic acid.

The process wherein acrylic acid is added to chlorosulfonic acid has several drawbacks, namely the low temperature addition (0°–10° C.) and long reaction time (20 hours), but more importantly it too requires slow heating to 80° C. to avoid the dangerous exotherm.

In addition, the reagent resulting from either of the latter two processes is not completely satisfactory. It is a brown liquid, relatively thin at temperatures above 35° C., very heavy but pourable at 25° C., but extremely viscous and not readily pourable at lower temperatures. It contains unreacted chlorosulfonic acid, and the low vapor pressure of this unreacted acid leads to acidic fuming when the reagent is poured. A further handling problem could develop during winter time storage at low temperatures, when the reagent could not be pumped or poured without heating the storage drums.

Hence, the search has begun for a safer and quicker process for preparing the anhydrous 3-chloro-2-sulfopropionic acid reagent and for preparing an aqueous reagent which is free of unreacted chlorosulfonic acid and pourable even at low temperatures and for a purer form of 3-chloro-2-sulfopropionic acid.

SUMMARY OF THE INVENTION

The above object is achieved by forming the reaction mixture by adding acrylic acid to chlorosulfonic acid maintained at about 45° to 130° C., whereby an exotherm is avoided and the reaction time is shortened. The reaction mixture is then maintained at about 60° to 130° C. for a time sufficient to complete the reaction, typically 2 to 6 hours. The chlorosulfonic acid is agitated during the addition and agitation is continued throughout the reaction.

An aqueous reagent is prepared from the resulting anhydrous reagent by adding sufficient water to the hot reagent, typically 1 to 3% water, to decompose the unreacted chlorosulfonic acid and adding sufficient additional water to dilute the reagent to a solids content of about 50 to 95% by weight, perferably 70–90%, based on total reagent solids. The viscosity of the aqueous reagent is thus reduced. The initial water addition should be carried out at between 65° and below 100° C. with agitation; the subsequent dilution may be carried out at lower temperatures. Crystalline 3-chloro-2-sulfopropionic acid can be recovered from aqueous reagents having a solids content above 80% and below 95%, preferably at 85–90% solids.

DESCRIPTION OF THE PREFERRED EMBODIMENTS

The reaction of acrylic acid and chlorosulfonic acid to produce 3-chloro-2-sulfopropionic acid is a complex reaction resulting in a mixture of various organic components and some inorganic components. The reagent resulting from this reaction typically contains, as the major organic components, predominantly 3-chloro-2-sulfopropionic acid and minor amounts of 2-sulfoacrylic acid and 3-chloropropionic acid. When prepared by the improved process of this invention, the anhydrous reagent, after decomposition of the unreacted chlorosulfonic acid, contains about 80–90% 3-chloro-2-sulfopropionic acid, up to 8% 2-sulfoacrylic acid, 7–20% 3-chloropropionic acid, and no acrylic acid. The organic composition of the aqueous reagent is similar to that of the anhydrous reagent.

In the improved process of this invention, acrylic acid is added to chlorosulfonic acid maintained at a temperature of about 45° to 130° C. The chlorosulfonic acid is agitated during the addition. The rate of addition may be regulated so that it is slow enough to maintain the temperature within the required temperature range or the chlorosulfonic acid may be externally cooled to allow for a more rapid addition of acrylic acid.

After the addition is complete, the reaction mixture is heated at about 60° to 130° C. to drive the reaction to completion. The reaction time will vary from about 2 to 6 hours depending on the temperature selected, with lower reaction temperatures requiring longer times to obtain good conversion to 3-chloro-2-sulfopropionic acid. Longer reaction times (e.g. 20 hours) are not precluded, but are unnecessary and do not improve the conversion. The preferred reaction conditions are 3 to 5 hours at 75° to 95° C.

In the process of this invention, the reaction mixture may be maintained during the acrylic acid addition at a temperature lower than the final reaction temperature, typically at 45° to 75° C. during the addition and at 75° to 130° C. during the reaction. Alternatively, the reaction mixture may be maintained at a higher temperature during the acrylic acid addition and allowed to drop to and maintained at a lower temperature for completion of the reaction, typically at 90° to 100° C. during the addition and at 80°-90° C. during the final reaction. Preferably the addition and final reaction temperatures are the same, typically about 75° to 95° C.

After completion of the acrylic acid addition at 45°-75° C., the reaction mixture may then be heated rapidly to the final reaction temperature without obtaining a large exothermic reaction. A short holding time of about 0.5 to 1 hour may be desirable if the addition temperature is at 45°-55° C. When the addition temperature is the same or higher than the reaction temperature (i.e. 75°-130° C.), no holding time is required and no exotherm is observed after the acrylic acid addition is completed.

This results in a safe process with the danger of a large exotherm having been eliminated and/or controlled by addition of the acrylic acid to the warm chlorosulfonic acid. In addition, since there is no excess acrylic acid present during formation of the reaction mixture, there is no possibility for the formation of polyacrylic acid and the resultant exotherm therefrom.

It is believed that the reaction takes place in two steps according to the sequence represented below:

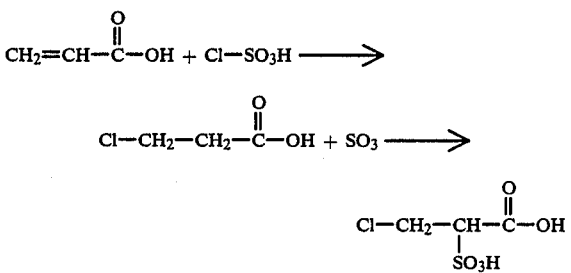

When the final reaction temperature is low (e.g. <60° C.), a much higher percentage of 3-chloropropionic acid is found in the reagent (20% vs. 11–12%).

Preferably, the anhydrous reagent prepared by this improved process, or by any prior art process using acrylic acid and chlorosulfonic acid, is treated with sufficient water to decompose any unreacted chlorosulfonic acid. Typically about 1-3% water is sufficient to destroy the unreacted acid when equimolar amounts of chlorosulfonic acid and acrylic acid are used. If an excess of chlorosulfonic acid (up to about 10% by weight) is used, it may require about 2 to 4% water to destroy the chlorosulfonic acid. The added water decomposes the chlorosulfonic acid into hydrogen chloride and sulfuric acid. The insoluble hydrogen chloride will cause serious foaming problems if the reagent is not maintained at a temperature high enough to reduce its viscosity and allow for safe escape of the gas. Addition at temperatures between 65° and below 100° C., preferably 75°-90° C., will eliminate the foaming problem. Foaming will also occur if the water is added too rapidly. Sufficient mixing must also be used to assure that the added water is not laying on the top of the more viscous organic layer. It may be possible to destroy the unreacted chlorosulfonic with aqueous solvents, providing the solvent is inert to the reagent's components and provided sufficient water is present in the solvent.

The reagent is then diluted with water to a solids content of 50 to 95% to provide an aqueous reagent of reduced viscosity (i.e. easily pourable at temperatures below 25° C.). The preferred dilution is to a solids content of about 70 to 90%, more preferably 85-90%. This dilution is preferably carried out at the same temperature as that used in the decomposition step and in the formation and reaction of the mixture, thus providing an efficient continuous process for preparing the aqueous reagent. However, dilution at a lower temperature is possible. Dilution at a later time is not precluded, but probably not necessary when the aqueous reagent has a solids content of about 70% or above as the reagent's storage stability is excellent, i.e. 6 months at 60° C. results in almost no change in the nuclear magnetic resonance spectrum (NMR) of the 85% solids reagent and only a very slight change due to hydrolysis of the acid to the corresponding alcohol with the 75% solids reagent. However, long term storage of the 50% solids reagent leads to substantial hydrolysis. In cases where dilute solutions are required, dilution to 70% solids with further dilution prior to use may be desirable. Dilution with solvents other than water is not precluded, but water is the preferred diluent unless an anhydrous reagent is desired. After dilution with water, the mixture may be vacuum stripped at temperatures of 30°-90° C. and pressures of 10-200 mm Hg to remove residual hydrochloric acid which tends to cause fuming in the unstripped mixture.

If desired, it may be possible to recover crystalline 3-chloro-2sulfopropionic acid by carrying out the dilution in two stages. About one half of the total amount of water necessary to make a 85% or 90% aqueous solution is added to the warm reaction mixture (cooled to 70° C. from the 80° C. reaction temperature). The mixture is then stirred at room temperature for an extended period of time (about 65 hours) and reheated to 70° C. prior to the addition of the remaining water. After storage at room temperature for several weeks, a large amount of amber crystals form. The brown liquid phase is decanted, and the crystals are washed rapidly with very cold water to remove the 2-sulfoacrylic acid and 3-chloropropionic acid. Hygroscopic white crystals are obtained.

It is possible to recover the crystalline acid from the aqueous reagent when the reagent has a solids content above about 80% and below about 95%, preferably 85-90%, by adding the water to the heated anhydrous reagent, as discussed hereinabove, cooling the mixture to room temperature, and seeding with a small amount of the crystalline acid. The water addition may be carried out in one step or in two steps as described above. At higher (95–100%) solids content, seeding produces no additional crystals, and the seed crystals remain unchanged. At lower solids (80% or less), the seed crystals dissolve. Refrigeration subsequent to seeding hastens the formation of crystals.

The following examples will more fully illustrate the embodiments of this invention. In the examples, all parts and percentages are given by weight and all temperatures are in degrees Celsius unless otherwise noted. The anhydrous and aqueous reagents are evaluated by nuclear magnetic resonance analysis, as well as by their reactivity with starch to form derivatives.

The following general procedures are used throughout the examples for the NMR analysis and the determination of the percentage of 2-sulfo-2-carboxyethyl ether substituent groups on the starch.

The proton NMR spectrum at 100 MHz is obtained from a 20% (by weight) solution of the reagent in $D_2O$. A capillary of tetramethylsilane is used as an external signal reference. The components present are listed in Table 1. The weight percentages given in the examples were calculated by electronic integration of the NMR spectrum. The small amount of unknown olefin and all inorganic components were ignored in these calculations.

maintain the mixture at about 60° C. After the addition was complete, the ice bath was removed. The temperature of the mixture dropped rapidly (within 1 min.) to about 45° C. The mixture was then heated over 10 mins. to 80° C. (about 1.2°/min.), held at 80° C. for 6 hrs., and cooled to room temperature (Reagent I-B). A sample was removed after 3 hrs. (Reagent I-A) for evaluation. The mixture was stirred both during the reagent addition and during the subsequent heating.

Reagent I-A contained 81.4% 3-chloro-2-sulfopropionic acid, 8.4% 2-sulfoacrylic acid, and 10.2% 3-chloropropionic acid, whereas Reagent I-B contained 81.1%, 9.1%, and 9.8% of the corresponding components. Neither reagent contained any acrylic acid.

The reactivity of the reagents was determined by their starch reactions. A total of 100 parts corn starch (two portions) was slurried in 125 parts water, and 8 parts of anhydrous reagents I-A and I-B were added, respectively. Calcium hydroxide was added until the pH was about 11.1 (usually required about 6.6–7.8 parts calcium hydroxide) and then 1.0 part of additional calcium hydroxide was added. The slurry was agitated at room temperature for 2 hrs., and the pH was then lowered to 3.0 with 10% aqueous hydrochloric acid. The starch products were filtered, washed with water (previously adjusted to pH 3.0), dried, and analyzed for percentage of 2-sulfocarboxyethyl ether substituent

TABLE I

| Compound | Chemical Shift | Pattern | Assignment |
| --- | --- | --- | --- |
| Cl—$CH_2$—$CH_2$—COOH | 3.4 | Triplet | —$\underline{CH_2}$—COOH |
| (3-Chloropropionic Acid) | 4.3 | Triplet | Cl—$\underline{CH_2}$— |
| Cl—$CH_2$—CH(COOH)($SO_3H$) (3-Chloro-2-sulfopropionic Acid) | 4.4–5.4 | Multiplet | —$\underline{CH_2}$— and —$\underline{CH}$— |
| $CH_2$=C(COOH)($SO_3H$) (2-Sulfoacrylic Acid) | 7.1 | Doublet | $CH_2$= |
| Unknown Olefin | 6.8 | Singlet | — |

The starch analyses are carried out by slurrying 5.000 g. of the starch derivative in 10 ml. of distilled water and then adding 25 ml. of a 0.1 N hydrochloric acid solution. The starch slurry is agitated for 30 minutes, filtered, and washed with distilled water until the starch is free of chloride ions as determined by the silver nitrate test. and 100 ml. of distilled water are added, followed by 200 ml. of hot distilled water. The resulting mixture is then heated with agitation in a boiling water bath for 10 minutes, after which it is removed from the bath and titrated while still hot with 0.1 N sodium hydroxide solution to a phenolphthlein pink endpoint.

EXAMPLE I

This example illustrates the preparation of the anhydrous 3-chloro-2-sulfopropionic acid reagent using the improved process of this invention.

Reagents I-A and I-B were prepared by slowly adding 37 parts acrylic acid over about 20 mins. to 65 parts chlorosulfonic acid in a flask. The reaction was exothermic; the mixture reached 60° C. in about 3–5 mins. It was cooled in an ice bath during the remainder of the chlorosulfonic acid addition (over about 15 mins.) to groups according the method previously described.

Starch derivative I-A contained 1.42% 2-sulfocarboxyethyl ether substituent groups, and starch derivative I-B contained 1.45%.

The results show that after the initial exotherm, which occurred during the chlorosulfonic acid addition, the reaction mixture can be rapidly heated to the final reaction temperature without a second exotherm occurring. It further shows that it is not necessary to use the longer reaction time at this temperature.

EXAMPLE II (comparative)

This example illustrates the exotherm problem encountered in using the prior art process of U.S. Pat. No. 2,895,987, wherein the chlorosulfonic acid is added to the acrylic acid.

Reagent I-A was prepared by placing 296 parts acrylic acid in a flask and then slowly adding 520 parts chlorosulfonic acid over 2 hrs. while maintaining the mixture's temperature at 25° C. by continuous cooling in an ice bath. The mixture was held for 10 mins. and then heated over 15 mins. to 40° C. An exotherm occurred; the mixture's temperature increased rapidly to 48° C. After cooling to 38° C. in an ice bath and holding for 5 mins., the mixture was heated over 55 mins. to 60° C. (about 0.4°/min.), then heated over 25 min. to 83° C. (about 1°/min.), maintained at 83° C. for 3.5 hrs., and cooled. The mixture was stirred during the chlorosulfonic acid addition and subsequent heating.

The resulting reagent contained 81.1% 3-chloro-2-sulfopropionic acid, 8.7% 2-sulfoacrylic acid, and 10.2% 3-chloropropionic acid. A starch derivative prepared as in Example I using this reagent contained 1.25% 2-sulfocarboxyethyl ether substitutent groups.

The results show that a potentially dangerous second exotherm (8° C.) occurs at about 40° C. and that this necessitates subsequent cooling and slow heating thereafter to 60° C. Although easily controlled in small scale laboratory reactions, this exotherm would be a much more serious problem during large scale commercial operations. It also shows that the anhydrous reagent prepared by this prior art process was no better than the anhydrous reagent prepared by the improved process of Example I with regards to the percentage of 3-chloro-2-sulfopropionic acid in the reagent.

EXAMPLE III (comparative)

This example illustrates the exotherm problem encountered in using the prior art process of the French journal, wherein acrylic acid is added to chlorosulfonic acid.

Reagents III-A and III-B were prepared by placing 65 parts chlorosulfonic acid in a flask and then adding 37 parts acrylic acid slowly over 22 mins. The reaction was exothermic. When the mixture reached 34° C. (within 1-2 mins.1, it was cooled in an ice bath and maintained at 33°-35° C. until the addition was completed. It was heated over 20 mins. to 43° C. (about 0.7°/min.) where an exotherm occurred, and the mixture's temperature rose to 46.5° C. Heating was stopped. When the temperature of the mixture had dropped to 46° C., it was heated over 5 mins. to 56° C. (about 2°/min.) and then over 10 mins. to 82° C. (about 2.6°/min.), maintained at 82° C. for 6 hrs., and cooled (III-B). A sample (III-A) was removed for evaluation at 3 hrs. The mixture was stirred during the acrylic acid addition and the subsequent reaction.

The resulting reagents were evaluated by their starch reactions using the method described in Example I. The precentage of 2-sulfocarboxyethyl ether substituent groups was 1.45% and 1.46% for III-A and III-B, respectively.

The results show that adding the acrylic acid to the chlorosulfonic acid, in contrast with the prior art process of Example II wherein chlorosulfonic acid is added to acrylic acid, did not eliminate the potentially dangerous second exotherm (3.5° C.) which occurred at about 40°-43° C. The small scale of this reaction (in contrast with that of Example II) resulted in more efficient air cooling so that the exotherm was somewhat smaller. The results also show that the anhydrous reagent prepared by this prior art process was no better in the starch reaction than the anhydrous reagent prepared by the improved process of Example 1.

EXAMPLE IV

This example illustrates the use of the improved process at varied addition temperatures with and without cooling. The mixtures were stirred during the addition and subsequent reaction at 80° C.

Reagent IV-A was prepared by placing 65 parts chlorosulfonic acid in a flask and slowly adding 37 parts acrylic acid. The reaction was exothermic and reached 45° C. in 2-4 mins. The addition was stopped and resumed after the temperature dropped. No cooling was used and the temperature was maintained at 45°-48° C. by controlling the rate of addition. The addition was completed in 89 mins. and the mixture was at 48° C. It was held for 30 mins. at 45° C. in a hot oil bath and then heated over 31 mins. to 80° C. (about 1.1°/min.). No exotherm occurred. It was maintained at 80° C. for 20 hrs. and then cooled. A sample was removed after 3 hrs. for evaluation.

Reagent IV-B was prepared in the same manner as Reagent IV-A except that the mixture was maintained at 45° C. during the addition by continuous cooling in an ice bath. The initial exotherm caused the temperature to reach 45° C. in about 2-4 mins. after 3.5 parts of acrylic acid had been added. The mixture was held for 30 mins. at 45° C. after the addition was completed and then heated to 80° C. over 45 mins. (about 0.7°/min.) and cooled. No exotherm occurred.

Reagent IV-C was prepared in the same manner as Reagent IV-A except that 653.3 parts of chlorosulfonic acid were used instead of 65 parts, and 402 parts of acrylic acid were used instead of 37 parts. The mixture was allowed to reach 60° C. (in about 10 mins.) before cooling was initiated. The total addition was completed in 30 mins. After removal from the ice bath, the mixture's temperature dropped 5° during 15 mins. It was then heated to 60° C. in about 3 mins. (1.7°/min.), held for 1 hr. with stirring, heated over 20 mins. to 80° C. (1°/min.), and then cooled. No exotherm occurred.

The reagents were evaluated as in Example I. The results are given in Table II.

The results show that the temperature can be controlled without cooling by adjusting the addition rate of acrylic acid and that the addition can be carried out at a temperature as low as 45° C. without an

TABLE II

| Reagent | Reaction Conditions | | NMR Analysis | | | | Starch Reaction |
|---|---|---|---|---|---|---|---|
| | Addition Temperature (°C.) | Time at 80° C. (hrs.) | CSPA[1] (%) | SA[2] (%) | CPA[3] (%) | AA[4] (%) | 2-Sulfocarboxy-ethyl Ether (%) |
| IV-A | 44 | 3 | — | — | — | — | 1.43 |
| IV-A | 44 | 20 | — | — | — | — | 1.43 |
| IV-B | 45 | 3 | 79.6 | 8.6 | 11.7 | 0 | 1.51 |
| IV-B | 45 | 20 | 84.2 | 7.4 | 8.3 | 0 | 1.45 |
| IV-C | 60 | 3 | 81.0 | 4.0 | 16.0 | 0 | 1.51 |

[1] 3-Chloro-2-sulfopropionic acid
[2] 2-Sulfoacrylic acid
[3] 3-Chloropropionic acid
[4] Acrylic acid The starch is then quantitatively transferred to a large beaker exotherm occurring during the subsequent heating to the final reaction temperature. It also shows that it is not necessary to carry out the reaction for longer than 3 hrs. at 80° C. It further shows that the process can be scaled up (tenfold increase in preparation of Reagent IV-C) without difficulty.

EXAMPLE V

This example illustrates the use of the improved process of Example I at other addition and reaction temperatures to prepare the improved aqueous reagents.

Reagents V-A to V-F were prepared and evaluated using the methods described in Example I except that Reagents V-C and V-D were held for 1 hr. at the addition temperature prior to heating to the final reaction temperature. Water was added at the end of the reaction time to form an 85% solids solution, based on total reagent solids. The data is summarized in Table III.

TABLE III

| Reagent | Acrylic Acid Addition Temperature (°C.) | Time (hr.) | Reaction Conditions Temperature (°C.) | Time (hr.) | NMR$^a$ Analysis CSPA$^b$ (%) | CPA$^c$ (%) | Starch Reaction$^d$ 2-Sulfocarboxy-ethyl Ether (%) |
|---|---|---|---|---|---|---|---|
| V-A | 60 | 1 | 60 | 4 | 79.5 | 20.5 | 1.18 |
| V-B | 80 | 1 | 80 | 4 | 88.8 | 11.2 | 1.36 |
| V-C | 60$^e$ | 1 | 80 | 3 | 88.1 | 11.9 | 1.28 |
| V-D | 60 | 1 | 100 | 3 | — | — | 1.30 |
| V-E | 110 | 0.5 | 110 | 4 | — | — | 1.46 |
| V-F | 130 | 0.5 | 130 | 4 | — | — | 1.15 |

$^a$Trace amounts of 2-sulfoacrylic acid were observed but were not measurable.
$^b$3-Chloro-2-sulfopropionic acid
$^c$3-Chloropropionic acid
$^d$9.4% Aqueous reagent on corn starch (8.0 parts dry basis)
$^e$10% Excess chlorosulfonic acid (38.9 parts/21.8 parts acrylic acid vs. 35.4 parts/21.8 parts)

The results show that the addition and reaction can be done at the same temperature and that addition and reaction temperatures as high as 130° C. can be used in the improved process. It also shows that reaction at a temperature below 80° C. does not provide as good a yield of 3-chloro2-sulfopropionic acid as reaction at the higher temperatures.

EXAMPLE VI

This example describes the preparation of the anhydrous reagent by the improved process using a higher addition temperature than the subsequent reaction temperature.

The addition should be carried out as in Example I except that the temperature is allowed to reach 100° C. and maintained at 100° C. during the addition. The temperature is then allowed to drop back to 80° C. after the addition is completed and then maintained at 80° C. for about 3 hrs. to complete the reaction.

EXAMPLE VII

This example illustrates the preparation of the improved anhydrous reagent and the aqueous reagent. It compares their composition and starch reactivity.

Part A - Decomposition of Unreacted Chlorosulfonic Acid

An anhydrous 3-chloro-2-sulfopropionic acid reagent (VII-A) was prepared according to the improved process of Example 1. A total of about 3 parts of water was added slowly with stirring to 85 parts of the anhydrous reagent while the temperature was maintained at 27, 40, 60, 70, and 80° C. during the addition. Heat evolution and foaming problems developed at the lower addition temperatures. As the temperature at which the water was added was increased, the foaming problem decreased. Starting the water addition at 70° C. and keeping the rate of addition slow resulted in elimination of the foaming problem both in the laboratory reaction and in a larger scale (25 lb.) pilot plant reaction.

Part B - Dilution of The Anhydrous Reagent

A series of aqueous reagents (VII-B to VII-E) were prepared by diluting anhydrous 3-chloro-2-sulfopropionic acid reagents (prepared according to the improved process of Example I) with sufficient water to give the indicated solids content. The dilution was carried out at various temperatures and it resulted in decomposition of the unreacted chlorosulfonic acid.

The composition and reactivity of freshly prepared anhydrous reagent (VII-A) was compared with that of the freshly diluted aqueous reagents (VII-B to VII-E). The starch reactions and evaluations were carried out as in Example I. The results are given in Table IV.

TABLE IV

| Reagent | Diluent | Dilution Conditions Temperature (°C.) | Final Solids$^a$ (%) | NMR Analysis CSPA$^b$ (%) | SA$^c$ (%) | CPA$^d$ (%) | Starch Reaction 2-Sulfocarboxy-ethyl Ether (%) |
|---|---|---|---|---|---|---|---|
| VII-A | None | — | 100 | 84.8 | 7.8 | 7.4 | 1.23 |
| VII-B | Water | 70 | 95 | — | — | — | 1.40 |
| VII-C$^e$ | Water | 80 | 85 | 90.6 | 0.8 | 8.6 | 1.27 |
| VII-D | Water | 40 | 83 | 87.2 | 3.5 | 9.3 | 1.29 |
| VII-E | Water | 70 | 83 | 88.1 | 2.6 | 9.3 | 1.33 |

$^a$Based on total reagent solids
$^b$3-Chloro-2-sulfopropionic acid
$^c$2-Sulfoacrylic acid
$^d$3-Chloropropionic acid
$^e$Prepared in the pilot plant, all others prepared in laboratory.

The Brookfield viscosity of Reagent VII-C, measured at 20° C. using a #3 spindle, was 1400 cps.

The results show that the aqueous reagents had a NMR spectrum similar to that of the anhydrous reagent and that they were equivalent in their starch reactions. It also shows that the final dilution can be carried out at temperatures as low as 40° C. and that the viscosity was reduced to an acceptable level.

EXAMPLE VIII

This example demonstrates the excellent storage stability of the high solids aqueous reagent.

Part A

Aqueous reagent VII-C of Example VII (85% solids) was stored at room temperature and at 60° C. for over 6 months. Aliquots were removed at the indicated times and evaluated by their starch reactions. The reactions were carried out in the same manner as in Example I except that 9.4 parts (8.0 parts dry basis) of the reagent were used, and the amount of calcium hydroxide usually required to adjust the pH to about 11.1 was 8.7 parts instead of 6.6-7.8 parts. The data is summarized in Table V.

TABLE V

| Storage Conditions (days at about 24° C.) | Starch Reaction 2-Sulfocarboxy-ethyl Ether (%) | Storage Conditions (days at 60° C.) | Starch Reaction 2-Sulfocarboxy-ethyl Ether (%) |
| --- | --- | --- | --- |
| 0 | 1.3 | 0 | 1.4 |
| 15 | 1.3 | 14 | 1.3 |
| 53 | 1.4 | 50 | 1.4 |
| 78 | 1.4 | 77 | 1.5 |
| 150 | 1.5 | 160 | 1.4 |
| 182 | 1.5 | 209 | 1.3 |

Analysis of the reagent by NMR indicated that there was essentially no change in the NMR spectrum with time except for a very slight amount of hydrolysis of 3-chloro-2-sulfopropionic acid to the corresponding alcohol. The results show that the reagent was very stable during storage, even accelerated storage at 60° C. for over 6 months.

Part B

An aqueous reagent (85% solids) was prepared using the procedure of Example I and cooled to room temperature; portions were further diluted with water to 75% and 50% solids and stored at room temperature for 6 months. Analysis of the reagent by NMR indicated that there was esentially no change in the NMR spectum with time for the 75% solids reagent except for the very slight amount of hydrolysis noted in Part A. However, there was substantial hydrolysis of the 50% solids reagent, with about half of the 3-chloro-2-sulfopropionic acid hydrolyzing to the corresponding alcohol.

The excellent storage stability of the reagent at 75% solids and above is surprising as one would have expected the presence of water (25%), over a long period of time, to have hydrolyzed the reactive chlorine in the reagent as it did at 50% solids.

EXAMPLE IX

This example describes the isolation of crystalline 3-chloro-2sulfopropionic acid.

A total of 402.0 parts acrylic acid was added slowly to 653.3 parts chlorosulfonic acid. The temperature increased during the addition, and the reaction mixture was cooled in an ice bath to maintain the temperature at 60° C. throughout the addition. After the addition was completed, the mixture was stirred for 1 hr. at 60° C., heated to 80° C., and maintained at 80° C. for 3 hrs. The mixture was then cooled to 70° C., and about 90 parts water were added. It was stirred for 66 hrs. at room temperature (about 24° C.), reheated to 70° C., and 90 parts water were added to give 85% solids. NMR analysis indicated that the organic components consisted of 84% 3-chloro-2-sulfopropionic acid, 2% 2-sulfoacrylic acid, and 14% 3-chloropropionic acid.

After being stored at room temperature for 4 weeks, a large amount of amber crystals had formed. The liquid phase was decanted. A portion of the crystals was washed quickly with very cold water until colorless and then analyzed. Another portion of the crystals was washed several times with very cold water until colorless, and the melting point was determined. NMR analysis indicated that the crystals were 97.7% 3-chloro-2-sulfopropionic acid and 2.3% chloropropionic acid. They were hygroscopic and had a melting point of 62°-70° C.

The above experiment was repeated in the identical manner except the water was reduced to 60 parts in each water addition step to give 90% solids. Crystals formed after 6 weeks storage at room temperature.

EXAMPLE X

This example describes additional methods for isolating the crystalline 3-chloro-2-sulfopropionic acid.

Anhydrous (100% solid) and aqueous (50-95% solids) 3-chloro-2sulfopropionic acid reagents were prepared according to the methods of Examples I and IX and stored at room temperature (R.T.) or in a refrigerator for the time indicated in Table VI. From 1-2.5% by weight of seed crystals of the pure 3-chloro-2-sulfopropionic acid of Example IX were added to the various reagents; duplicate samples containing no seed crystals were also observed.

Data on the increase in or disappearance of crystals in the seeded reagents indicate that the crystals can only be formed at above 80% solids and below 95% solids, with crystals forming at both 85 and 90% solids. At higher solids (95-100%) the seed crystals remained unchanged and no additional crystals appeared. At lower solids (50-80%) the seed crystals dissolved and no crystals formed. Data on the appearance of crystals in the non-seeded reagent showed that crystallization only occurred in the 85% solids reagent (refrigerated for 19-27 days and stored for an additional 92-156 days at room temperature).

Now that the preferred embodiments of the present invention have been described in detail, various modifications and improvements thereon will become readily apparent to those skilled in the art. Accordingly, the spirit and a scope of the invention are to be limited only by the appended claims, and not by the foregoing specification.

TABLE VI

| Reagent* (% solids) | Crystalline 3-Chloro-2-Sulfopropionic Acid (% added) | Storage Conditions | Time** | Crystal Formation |
|---|---|---|---|---|
| 100 | 1.0 | Refrigerated | 23 | None (seed crystals unchanged) |
|  |  | R.T. | 101 | None (seed crystals unchanged) |
| 95 | 1.0 | Refrigerated | 23 | None (seed crystals slightly larger) |
|  |  | R.T. | 101 | None (seed crystals slightly larger) |
| 90 | 1.0 | Refrigerated | 23 | Many crystals |
|  |  | R.T. | 101 | Very many crystals |
| 85 | 1.0 | Refrigerated | 23 | Very many crystals |
|  |  | R.T. | 101 | Very many crystals |
| 100, 95, 90 & 85 | 0 | Refrigerated | 23 | None |
|  |  | R.T. | 101 | None |
| 85 | 1.1 | R.T. | 8 | Some crystals |
|  |  | R.T. | 19 | Many crystals |
|  |  | R.T. | 210 | Very many crystals |
| 85 | 1.0 | Refrigerated | 8 | Many crystals |
|  |  | Refrigerated | 19 | Many crystals |
|  |  | Refrigerated | 210 | Very many crystals |
| 85 | 0 | Refrigerated | 8 | None |
|  |  | R.T. | 183 | Some crystals |
|  |  | Refrigerated | 19 | None |
|  |  | R.T. 183 | 183 | Some crystals |
| 85 | 1.25 | Refrigerated | 2 | Many crystals |
|  |  | R.T. | 195 | Very many crystals |
| 80 | 2.50 | Refrigerated | 2 | None (seed crystals unchanged) |
|  |  | R.T. | 195 | None (seed crystals unchanged) |
| 75 | 1.25 | Refrigerated | 2 | None (seed crystals dissolved) |
|  |  | R.T. | 195 | None (seed crystals dissolved) |
| 50 | 2.50 | Refrigerated | 2 | None (seed crystals dissolved) |
|  |  | R.T. | 195 | None (seed crystals dissolved) |
| 85, 80, 75, and 50 | 0 | Refrigerated | 2 | None |
|  |  | R.T. | 195 | None |

*Preparation of the first set (85–100%) was according to the method of Example I; preparation of the other sets (85% and 50–85%) was according to the method of Example II.
**Total time from reagent preparation and seeding, if any.

What is claimed is:

1. A composition of matter, comprising crystalline 3-chloro-2-sulfo-propionic acid.

2. A method for isolating crystalline 3-chloro-2-sulfo-propionic acid by seeding an aqueous 3-chloro-2-sulfo-propionic acid reagent which comprises the steps of:
   (a) forming and heating a reaction mixture of chlorosulfonic acid and acrylic acid to form an anhydrous 3-chloro-2-sulfopropionic acid reagent;
   (b) adding water to said anhydrous reagent maintained at about 65° C. and below 100° C. in an amount sufficient to decompose said unreacted chlorosulfonic acid and dilute said anhydrous reagent to an aqueous reagent having a solids content of above about 80% and below about 95% by weight, based on total reagent solids; and
   (c) cooling said aqueous reagent to room temperature prior to said seeding.

3. The method of claim 2, wherein said anhydrous reagent is diluted to an aqueous reagent having a solids content of about 85 to 90% and refrigerated subsequent to said seeding.

* * * * *

UNITED STATES PATENT AND TRADEMARK OFFICE
CERTIFICATE OF CORRECTION

PATENT NO. : 4,732,710

DATED : March 22, 1988

INVENTOR(S) : Martin M. Tessler, Dennis V. Neigel

It is certified that error appears in the above-identified patent and that said Letters Patent are hereby corrected as shown below:

Col. 9, lines 1-2, delete the phrase "The starch is then quantitatively transferred to a large beaker".

Col. 10, line 11, "Example 1" should read -- Example I --.

Col. 13, line 33, in footnote ** to Table VI, insert -- (in days) -- after "time".

Signed and Sealed this

Thirteenth Day of September, 1988

Attest:

DONALD J. QUIGG

*Attesting Officer*    *Commissioner of Patents and Trademarks*